(12) United States Patent
Lichtenstein et al.

(10) Patent No.: US 8,449,605 B2
(45) Date of Patent: May 28, 2013

(54) METHOD FOR ANCHORING A MITRAL VALVE

(75) Inventors: Samuel Victor Lichtenstein, Vancouver (CA); Daniel Gelbart, Vancouver (CA)

(73) Assignee: Kardium Inc., Richmond (CA)

( * ) Notice: Subject to any disclaimer, the term of this patent is extended or adjusted under 35 U.S.C. 154(b) by 1683 days.

(21) Appl. No.: 11/475,978

(22) Filed: Jun. 28, 2006

(65) Prior Publication Data

US 2008/0004697 A1 Jan. 3, 2008

(51) Int. Cl.
*A61F 2/24* (2006.01)

(52) U.S. Cl.
USPC .......... 623/2.11; 623/2.36; 623/2.37; 623/2.1

(58) Field of Classification Search
USPC ................ 623/2.24, 2.1–2.19, 2.36, 2.37
IPC ........................................... A61F 2/24
See application file for complete search history.

(56) References Cited

U.S. PATENT DOCUMENTS

| | | | |
|---|---|---|---|
| 3,132,438 A | 5/1964 | Ward et al. ............... 43/53.5 |
| 4,114,202 A | 9/1978 | Roy et al. | |
| 4,164,046 A | 8/1979 | Cooley ........................... 3/1.5 |
| 4,240,441 A | 12/1980 | Khalil ........................ 128/692 |
| 4,261,342 A | 4/1981 | Aranguren Duo ......... 128/1 R |
| 4,263,680 A | 4/1981 | Reul et al. | |
| 4,490,859 A | 1/1985 | Black et al. | |
| 4,543,090 A | 9/1985 | McCoy .......................... 604/95 |
| 4,794,912 A | 1/1989 | Lia ................................ 128/4 |
| 4,850,957 A | 7/1989 | Summers .................... 604/22 |
| 4,890,602 A | 1/1990 | Hake ............................. 128/4 |
| 4,890,612 A | 1/1990 | Kensey ...................... 606/213 |
| 4,893,613 A | 1/1990 | Hake ............................. 128/4 |
| 4,921,499 A | 5/1990 | Hoffman et al. ............ 623/16 |
| 5,021,059 A | 6/1991 | Kensey et al. ............. 606/213 |
| 5,047,047 A | 9/1991 | Yoon .......................... 606/216 |
| 5,100,418 A | 3/1992 | Yoon et al. ................. 606/139 |
| 5,104,399 A | 4/1992 | Lazarus ........................ 623/1 |
| 5,122,137 A | 6/1992 | Lennox ....................... 606/40 |
| 5,156,609 A | 10/1992 | Nakao et al. .............. 606/142 |
| 5,192,314 A | 3/1993 | Daskalakis ................... 623/3 |
| 5,258,000 A | 11/1993 | Gianturco ................. 606/151 |
| 5,312,435 A | 5/1994 | Nash et al. ................ 606/213 |

(Continued)

FOREIGN PATENT DOCUMENTS

| | | |
|---|---|---|
| WO | 90/15582 | 12/1990 |
| WO | 01/78625 | 10/2001 |

(Continued)

OTHER PUBLICATIONS

U.S. Appl. No. 10/690,131, filed Oct. 20, 2003, Lichtenstein.

(Continued)

*Primary Examiner* — Thomas J Sweet
*Assistant Examiner* — Jason-Dennis Stewart
(74) *Attorney, Agent, or Firm* — Seed IP Law Group PLLC (57) ABSTRACT

An artificial mitral valve is anchored in the left atrium by placing the valve between the annulus of the natural mitral valve and an artificial annulus. The artificial annulus is formed by inserting a tool into the coronary sinus, and adjusting the tool to force the wall of the left atrium to form an annulus above the artificial valve, this locking it in place and forming a hemostatic seal.

16 Claims, 7 Drawing Sheets

U.S. PATENT DOCUMENTS

| | | | |
|---|---|---|---|
| 5,320,632 A | 6/1994 | Heidmueller | 606/144 |
| 5,364,408 A | 11/1994 | Gordon | 606/144 |
| 5,366,443 A | 11/1994 | Eggers et al. | 604/114 |
| 5,366,459 A | 11/1994 | Yoon | 606/151 |
| 5,368,601 A | 11/1994 | Sauer et al. | 606/144 |
| 5,374,275 A | 12/1994 | Bradley et al. | 606/144 |
| 5,450,860 A | 9/1995 | O'Connor | 128/898 |
| 5,478,353 A | 12/1995 | Yoon | 606/213 |
| 5,531,760 A | 7/1996 | Alwafaie | 606/216 |
| 5,593,424 A | 1/1997 | Northrup, III | 606/232 |
| 5,713,896 A | 2/1998 | Nardella | 606/50 |
| 5,716,397 A | 2/1998 | Myers | 623/2 |
| 5,720,726 A | 2/1998 | Marcadis et al. | 604/96 |
| 5,728,114 A | 3/1998 | Evans et al. | 606/148 |
| 5,782,861 A | 7/1998 | Cragg et al. | 606/216 |
| 5,800,495 A | 9/1998 | Machek et al. | 607/116 |
| 5,824,066 A | 10/1998 | Gross | 623/2 |
| 5,836,990 A | 11/1998 | Li | 607/28 |
| 5,865,791 A | 2/1999 | Whayne et al. | 604/49 |
| 5,919,207 A | 7/1999 | Taheri | 606/219 |
| 5,961,440 A | 10/1999 | Schweich, Jr. et al. | 600/16 |
| 5,964,782 A | 10/1999 | Lafontaine et al. | 606/213 |
| 5,984,950 A | 11/1999 | Cragg et al. | 606/216 |
| 6,001,069 A | 12/1999 | Tachibana et al. | 601/2 |
| 6,024,096 A | 2/2000 | Buckberg | 128/898 |
| 6,074,417 A | 6/2000 | Peredo | 623/2 |
| 6,104,944 A | 8/2000 | Martinelli | 600/424 |
| 6,113,610 A | 9/2000 | Poncet | 606/139 |
| 6,203,554 B1 | 3/2001 | Roberts | 606/144 |
| 6,210,432 B1 | 4/2001 | Solem et al. | 623/1.15 |
| 6,221,103 B1 | 4/2001 | Melvin | 623/3.1 |
| 6,221,104 B1 | 4/2001 | Buckberg et al. | 623/3.1 |
| 6,241,747 B1 | 6/2001 | Ruff | 606/216 |
| 6,248,124 B1 | 6/2001 | Pedros et al. | 606/213 |
| 6,258,258 B1 | 7/2001 | Sartori et al. | 208/263 |
| 6,287,321 B1 | 9/2001 | Jang | 606/200 |
| 6,304,769 B1 | 10/2001 | Arenson et al. | 600/424 |
| 6,306,135 B1 | 10/2001 | Ellman et al. | 606/45 |
| 6,332,864 B1 | 12/2001 | Schweich, Jr. et al. | 600/16 |
| 6,346,105 B1 | 2/2002 | Tu et al. | 606/41 |
| 6,358,258 B1 | 3/2002 | Arcia et al. | 606/139 |
| 6,358,277 B1 | 3/2002 | Duran | 623/2.12 |
| 6,360,749 B1 | 3/2002 | Jayaraman | 128/898 |
| 6,379,366 B1 | 4/2002 | Fleischman et al. | 606/139 |
| 6,391,048 B1 | 5/2002 | Ginn et al. | 606/213 |
| 6,391,054 B2 | 5/2002 | Carpentier et al. | 623/2.37 |
| 6,402,680 B2 | 6/2002 | Mortier et al. | 600/16 |
| 6,402,781 B1 | 6/2002 | Langberg et al. | 623/2.36 |
| 6,406,420 B1 | 6/2002 | McCarthy et al. | 600/16 |
| 6,409,760 B1 | 6/2002 | Melvin | 623/3.1 |
| 6,416,459 B1 | 7/2002 | Haindl | 600/37 |
| 6,436,052 B1 | 8/2002 | Nikolic et al. | 600/529 |
| 6,450,171 B1 | 9/2002 | Buckberg et al. | 128/898 |
| 6,475,223 B1 | 11/2002 | Werp et al. | 606/108 |
| 6,485,489 B2 | 11/2002 | Teirstein et al. | 606/41 |
| 6,506,210 B1 | 1/2003 | Kanner | 606/213 |
| 6,537,198 B1 | 3/2003 | Vidlund et al. | 600/16 |
| 6,537,314 B2 | 3/2003 | Langberg et al. | 623/2.36 |
| 6,540,670 B1 | 4/2003 | Hirata et al. | 600/152 |
| 6,551,312 B2 | 4/2003 | Zhang et al. | 606/41 |
| 6,569,160 B1 | 5/2003 | Goldin et al. | 606/41 |
| 6,569,198 B1 | 5/2003 | Wilson et al. | 623/2.37 |
| 6,575,971 B2 | 6/2003 | Hauck et al. | 606/52 |
| 6,589,208 B2 | 7/2003 | Ewers et al. | 604/104 |
| 6,626,930 B1 | 9/2003 | Allen et al. | 606/213 |
| 6,632,238 B2 | 10/2003 | Ginn et al. | 606/213 |
| 6,662,034 B2 | 12/2003 | Segner et al. | 600/373 |
| 6,676,685 B2 | 1/2004 | Pedros et al. | 606/213 |
| 6,723,038 B1 | 4/2004 | Schroeder et al. | 600/16 |
| 6,726,704 B1 | 4/2004 | Loshakove et al. | 606/213 |
| 6,726,716 B2 | 4/2004 | Marquez | 623/2.36 |
| 6,743,241 B2 | 6/2004 | Kerr | 606/144 |
| 6,749,622 B2 | 6/2004 | McGuckin, Jr. et al. | 606/213 |
| 6,760,616 B2 | 7/2004 | Hoey et al. | 600/547 |
| 6,780,197 B2 | 8/2004 | Roe et al. | 606/213 |
| 6,797,001 B2 | 9/2004 | Mathis et al. | 623/2.37 |
| 6,800,090 B2 | 10/2004 | Alferness et al. | 623/2.36 |
| 6,852,076 B2 | 2/2005 | Nikolic et al. | 600/37 |
| 6,855,143 B2 | 2/2005 | Davison et al. | 606/41 |
| 6,890,353 B2 | 5/2005 | Cohn et al. | 623/2.37 |
| 6,899,674 B2 | 5/2005 | Viebach et al. | 600/152 |
| 6,908,478 B2 | 6/2005 | Alferness et al. | 623/1.11 |
| 6,949,122 B2 | 9/2005 | Adams et al. | 623/2.36 |
| 6,960,229 B2 | 11/2005 | Mathis et al. | 623/2.36 |
| 6,986,775 B2 | 1/2006 | Morales et al. | 606/139 |
| 6,989,028 B2 | 1/2006 | Lashinski et al. | 623/2.37 |
| 6,991,649 B2 | 1/2006 | Sievers | 623/2.23 |
| 6,994,093 B2 | 2/2006 | Murphy et al. | 128/898 |
| 6,997,951 B2 | 2/2006 | Solem et al. | 623/2.37 |
| 7,025,776 B1 | 4/2006 | Houser et al. | 606/213 |
| 7,050,848 B2 | 5/2006 | Hoey et al. | 600/547 |
| 7,052,487 B2 | 5/2006 | Cohn et al. | 604/509 |
| 7,144,363 B2 | 12/2006 | Pai et al. | 600/16 |
| 7,166,127 B2 | 1/2007 | Spence et al. | 623/2.37 |
| 7,177,677 B2 | 2/2007 | Kaula et al. | 600/546 |
| 7,186,210 B2 | 3/2007 | Feld et al. | 600/16 |
| 7,189,202 B2 | 3/2007 | Lau et al. | 600/37 |
| 7,279,007 B2 | 10/2007 | Nikolic et al. | 623/11.11 |
| 7,300,435 B2 | 11/2007 | Wham et al. | 606/34 |
| 7,303,526 B2 | 12/2007 | Sharkey et al. | 600/37 |
| 7,374,530 B2 | 5/2008 | Schaller | 600/16 |
| 7,399,271 B2 | 7/2008 | Khairkhahan | 600/16 |
| 7,431,726 B2 | 10/2008 | Spence et al. | 606/151 |
| 7,452,325 B2 | 11/2008 | Schaller | 600/37 |
| 7,507,252 B2* | 3/2009 | Lashinski et al. | 623/2.37 |
| 7,582,051 B2 | 9/2009 | Khairkhahan et al. | 600/16 |
| 2001/0003158 A1 | 6/2001 | Kensey et al. | 606/213 |
| 2001/0005787 A1 | 6/2001 | Oz et al. | 606/142 |
| 2001/0018611 A1 | 8/2001 | Solem et al. | 623/2.37 |
| 2001/0020126 A1 | 9/2001 | Swanson et al. | 600/407 |
| 2001/0044568 A1 | 11/2001 | Langberg et al. | 600/37 |
| 2002/0016628 A1 | 2/2002 | Langberg et al. | 623/2.36 |
| 2002/0026092 A1 | 2/2002 | Buckberg et al. | 600/37 |
| 2002/0055775 A1 | 5/2002 | Carpentier et al. | 623/2.17 |
| 2002/0082621 A1 | 6/2002 | Schurr et al. | 606/151 |
| 2002/0087173 A1 | 7/2002 | Alferness et al. | |
| 2002/0115944 A1 | 8/2002 | Mendes et al. | 600/594 |
| 2002/0161394 A1 | 10/2002 | Macoviak et al. | 606/200 |
| 2002/0169359 A1 | 11/2002 | McCarthy et al. | 600/16 |
| 2002/0169360 A1 | 11/2002 | Taylor et al. | 600/37 |
| 2002/0169504 A1 | 11/2002 | Alferness et al. | 623/2.36 |
| 2002/0183836 A1 | 12/2002 | Liddicoat et al. | 623/2.11 |
| 2002/0183841 A1 | 12/2002 | Cohn et al. | |
| 2002/0188170 A1 | 12/2002 | Santamore et al. | 600/37 |
| 2002/0198603 A1 | 12/2002 | Buckberg et al. | 623/23.71 |
| 2003/0045896 A1 | 3/2003 | Murphy et al. | 606/191 |
| 2003/0050682 A1 | 3/2003 | Sharkey et al. | 607/126 |
| 2003/0050685 A1 | 3/2003 | Nikolic et al. | 623/1.11 |
| 2003/0069570 A1 | 4/2003 | Witzel et al. | 606/28 |
| 2003/0069636 A1 | 4/2003 | Solem et al. | 623/2.37 |
| 2003/0078465 A1 | 4/2003 | Pai et al. | 600/16 |
| 2003/0078652 A1 | 4/2003 | Sutherland | 623/2.12 |
| 2003/0078671 A1 | 4/2003 | Lesniak et al. | 623/23.64 |
| 2003/0105384 A1 | 6/2003 | Sharkey et al. | 600/16 |
| 2003/0105520 A1 | 6/2003 | Alferness et al. | |
| 2003/0109770 A1 | 6/2003 | Sharkey et al. | 600/16 |
| 2003/0149333 A1 | 8/2003 | Alferness | 600/16 |
| 2003/0163191 A1 | 8/2003 | Nikolic et al. | 623/1.11 |
| 2003/0220667 A1 | 11/2003 | van der Burg et al. | 606/200 |
| 2003/0229395 A1 | 12/2003 | Cox | 623/2.36 |
| 2004/0002626 A1 | 1/2004 | Feld et al. | 600/37 |
| 2004/0054279 A1 | 3/2004 | Hanley | 600/424 |
| 2004/0133273 A1 | 7/2004 | Cox | 623/2.11 |
| 2004/0138529 A1 | 7/2004 | Wiltshire et al. | 600/144 |
| 2004/0138744 A1 | 7/2004 | Lashinski et al. | 623/2.36 |
| 2004/0153146 A1 | 8/2004 | Lashinski et al. | 623/2.36 |
| 2004/0158321 A1 | 8/2004 | Reuter et al. | |
| 2004/0186566 A1 | 9/2004 | Hindrichs et al. | 623/2.37 |
| 2004/0215232 A1 | 10/2004 | Belhe et al. | 606/213 |
| 2004/0243170 A1 | 12/2004 | Suresh et al. | 606/198 |
| 2004/0249408 A1 | 12/2004 | Murphy et al. | 606/198 |
| 2004/0249453 A1 | 12/2004 | Cartledge et al. | 623/2.37 |
| 2004/0260390 A1* | 12/2004 | Sarac et al. | 623/1.24 |
| 2004/0267358 A1 | 12/2004 | Reitan | 623/2.37 |
| 2005/0004668 A1 | 1/2005 | Aklog et al. | 623/2.36 |
| 2005/0015109 A1 | 1/2005 | Lichtenstein | 606/200 |
| 2005/0038509 A1 | 2/2005 | Ashe | 623/2.36 |

| | | | |
|---|---|---|---|
| 2005/0054938 A1 | 3/2005 | Wehman et al. ............... 600/483 |
| 2005/0055089 A1 | 3/2005 | Macoviak et al. |
| 2005/0060030 A1 | 3/2005 | Lashinski et al. ............ 623/2.37 |
| 2005/0064665 A1 | 3/2005 | Han ............... 438/286 |
| 2005/0075727 A1 | 4/2005 | Wheatley ...................... 623/2.17 |
| 2005/0080402 A1 | 4/2005 | Santamore et al. ............... 606/1 |
| 2005/0096047 A1 | 5/2005 | Haberman et al. ............ 455/432.3 |
| 2005/0107723 A1 | 5/2005 | Wehman et al. ............... 600/595 |
| 2005/0107871 A1 | 5/2005 | Realyvasquez et al. ...... 623/2.11 |
| 2005/0125030 A1 | 6/2005 | Forsberg et al. ............... 606/213 |
| 2005/0137700 A1 | 6/2005 | Spence et al. ............... 623/2.36 |
| 2005/0149014 A1 | 7/2005 | Hauck et al. ...................... 606/41 |
| 2005/0149114 A1 | 7/2005 | Cartledge et al. ............ 606/213 |
| 2005/0154252 A1 | 7/2005 | Sharkey et al. ............... 600/37 |
| 2005/0177180 A1 | 8/2005 | Kaganov et al. ............... 606/151 |
| 2005/0177227 A1 | 8/2005 | Heim et al. ...................... 623/2.12 |
| 2005/0182365 A1 | 8/2005 | Hennemann et al. ........ 604/113 |
| 2005/0187620 A1 | 8/2005 | Pai et al. ...................... 623/2.37 |
| 2005/0197692 A1 | 9/2005 | Pai et al. ...................... 623/2.1 |
| 2005/0197693 A1 | 9/2005 | Pai et al. ...................... 623/2.1 |
| 2005/0197694 A1 | 9/2005 | Pai et al. ...................... 623/2.1 |
| 2005/0197716 A1 | 9/2005 | Sharkey et al. ............ 623/23.67 |
| 2005/0209636 A1 | 9/2005 | Widomski et al. ............ 606/213 |
| 2005/0216052 A1 | 9/2005 | Mazzocchi et al. ........... 606/200 |
| 2005/0216054 A1 | 9/2005 | Widomski et al. ............ 606/213 |
| 2005/0240249 A1 | 10/2005 | Tu et al. ...................... 607/96 |
| 2005/0251116 A1 | 11/2005 | Steinke et al. ...................... 606/8 |
| 2005/0267574 A1 | 12/2005 | Cohn et al. ................... 623/2.36 |
| 2006/0014998 A1 | 1/2006 | Sharkey et al. ............... 600/16 |
| 2006/0015002 A1 | 1/2006 | Moaddeb et al. ............... 600/37 |
| 2006/0015003 A1 | 1/2006 | Moaddes et al. ............... 600/37 |
| 2006/0015038 A1 | 1/2006 | Weymarn-Scharli ........ 600/585 |
| 2006/0025800 A1 | 2/2006 | Suresh ........................ 606/198 |
| 2006/0030881 A1 | 2/2006 | Sharkey et al. ............... 606/213 |
| 2006/0058871 A1 | 3/2006 | Zakay et al. ................. 623/2.18 |
| 2006/0135968 A1 | 6/2006 | Schaller ........................ 606/144 |
| 2006/0135970 A1 | 6/2006 | Schaller ........................ 606/152 |
| 2006/0173536 A1 | 8/2006 | Mathis et al. ................. 623/2.11 |
| 2006/0184242 A1 | 8/2006 | Lichtenstein ................. 623/2.37 |
| 2006/0199995 A1 | 9/2006 | Vijay ............................... 600/37 |
| 2006/0229491 A1 | 10/2006 | Sharkey et al. ................. 600/37 |
| 2006/0235286 A1 | 10/2006 | Stone et al. ................... 600/381 |
| 2006/0241334 A1 | 10/2006 | Dubi et al. ..................... 600/16 |
| 2006/0264980 A1 | 11/2006 | Khairkhahan et al. ........ 606/153 |
| 2006/0276683 A1 | 12/2006 | Feld et al. ...................... 600/16 |
| 2006/0281965 A1 | 12/2006 | Khairkhahan et al. .......... 600/37 |
| 2006/0293698 A1 | 12/2006 | Douk ........................... 606/142 |
| 2007/0016068 A1 | 1/2007 | Grunwald et al. ............ 600/468 |
| 2007/0118215 A1 | 5/2007 | Moaddeb ...................... 623/2.37 |
| 2007/0161846 A1 | 7/2007 | Nikolic et al. .................. 600/16 |
| 2007/0198058 A1 | 8/2007 | Gelbart et al. ................. 606/213 |
| 2007/0213578 A1 | 9/2007 | Khairkhahan et al. .......... 600/16 |
| 2007/0213815 A1 | 9/2007 | Khairkhahan et al. ......... 623/3.1 |
| 2007/0219460 A1 | 9/2007 | Goldenberg .................. 600/566 |
| 2007/0250160 A1 | 10/2007 | Rafiee ........................... 623/2.11 |
| 2007/0270688 A1 | 11/2007 | Gelbart et al. ................. 600/427 |
| 2008/0004643 A1 | 1/2008 | To et al. ......................... 606/159 |
| 2008/0004697 A1 | 1/2008 | Lichtenstein et al. ........ 623/2.11 |
| 2008/0033541 A1 | 2/2008 | Gelbart et al. ................. 623/2.11 |
| 2008/0045778 A1 | 2/2008 | Lichtenstein et al. .......... 600/16 |
| 2008/0071298 A1 | 3/2008 | Khairkhahan et al. ........ 606/151 |
| 2008/0086164 A1 | 4/2008 | Rowe ........................... 606/191 |
| 2009/0076597 A1 | 3/2009 | Dahlgren et al. ............... 623/2.1 |
| 2009/0287304 A1 | 11/2009 | Dahlgren et al. ............. 623/2.37 |

FOREIGN PATENT DOCUMENTS

| | | |
|---|---|---|
| WO | 03/015611 | 2/2003 |
| WO | 03/077800 | 9/2003 |
| WO | 2004/012629 | 2/2004 |
| WO | 2004/047679 | 6/2004 |
| WO | 2004/084746 | 10/2004 |
| WO | 2004/100803 | 11/2004 |
| WO | 2005/046520 | 5/2005 |
| WO | 2005/070330 | 8/2005 |
| WO | 2005/102181 | 11/2005 |
| WO | 2006/017809 | 2/2006 |
| WO | 2006/135747 | 12/2006 |
| WO | 2006/135749 | 12/2006 |
| WO | 2007/021647 | 2/2007 |
| WO | 2007/115390 | 10/2007 |

OTHER PUBLICATIONS

U.S. Appl. No. 11/400,260, filed Apr. 10, 2006, Lichtenstein.
U.S. Appl. No. 11/436,584, filed May 19, 2006, Gelbart et al.
U.S. Appl. No. 11/436,585, filed May 19, 2006, Gelbart et al.
U.S. Appl. No. 11/497,309, filed Aug. 2, 2006, Lichtenstein et al.
U.S. Appl. No. 12/120,195, filed May 13, 2008, Dahlgren et al.
Buchbinder, Maurice, MD, "Dynamic Mitral Valve Annuloplasty: A Reshapable Ring for Residual and Recurring MR," from the *Foundation for Cardiovascular Medicine*, La Jolla, CA. May 24, 2007.
Konings et al., "Development of an Intravascular Impedance Catheter for Detection of Fatty Lesions in Arteries," *IEEE Transactions on Medical Imaging*, 16(4):439-446, 1997.
Mack, "New Techniques for Percutaneous Repair of the Mitral Valve," *Heart Failure Review*, 11:259-268, 2006.
Otasevic et al., "First-in-Man Implantation of Left Ventricular Partitioning Device in a Patient With Chronic Heart Failure: Twelve-Month Follow-up," *Journal of Cardiac Failure* 13(7):517-520, 2007.
Sharkey et al., "Left Ventricular Apex Occluder. Description of a Ventricular Partitioning Device," *EuroIntervention* 2:125-127, 2006.
Stiles, et al., "Simulated Characterization of Atherosclerotic Lesions in the Coronary Arteries by Measurement of Bioimpedance," *IEE Transactions on Biomedical Engineering*, 50(7):916-921, 2003.
Tanaka et al., "Artificial SMA Valve for Treatment of Urinary Incontinence: Upgrading of Valve and Introduction of Transcutaneous Transformer," *Bio-Medical Materials and Engineering* 9:97-112, 1999.
Timek et al., "Septal-Lateral Annular Cinching ('SLAC') Reduces Mitral Annular Size Without Perturbing Normal Annular Dynamics," *Journal of Heart Valve Disease* 11(1):2-10, 2002.
Timek et al., "Septal-Lateral Annular Cinching Abolishes Acute Ischemic Mitral Regurgitation," *Journal of Thoracic and Cardiovascular Surgery*, 123(5):881-888, 2002.
Valvano et al., "Thermal Conductivity and Diffusivity of Biomaterials Measured with Self-Heated Thermistors," *International Journal of Thermodynamics*, 6(3):301-311, 1985.
Athanasuleas et al., "Surgical Anterior Ventricular Restoration for Ischemic Cardiomyopathy," *Operative Techniques in Thoracic and Cardiovascular Surgery* 7(2):66-75, May 2002.
Cardiac Implants, URL=http://nmtmedical.com/products/ci/index.htm, download date May 13, 2006, 1 page.
Cooley, "Ventricular Aneurysms and Akinesis," *Cleveland Clinic Quarterly* 45(1):130-132, 1978.
Dahlgren et al., "Medical Device, Kit and Method for Constricting Tissue or a Bodily Orifice, for Example a Mitral Valve," U.S. Appl. No. 61/278,232, filed Oct. 1, 2009, 215 pages.
Dahlgren et al., "Medical Device for Constricting Tissue or a Bodily Orifice, for Example a Mitral Valve," Office Action mailed Dec. 18, 2009, for U.S. Appl. No. 12/120,195, 9 pages.
David et al., "Postinfarction Ventricular Septal Rupture: Repair by Endocardial Patch with Infarct Exclusion," *Journal of Thoracic and Card Surgery* 110(5):1315-1322, 1995.
Dor et al., "Left Ventricular Aneurysm: A New Surgical Approach," *Thoracic Cardiovascular Surgery* 37:11-19, 1989.
Dor et al., "Late Hemodynamic Results After Left Ventricular Patch Repair Associated with Coronary Grafting in Patients with Postinfarction Akinetic or Dyskinetic Aneurysm of the Left Ventricle," *Journal of Thoracic and Cardiovascular Surgery* 110(5):1291-1301, 1995.
Dor, "Left Ventricular Aneurysms: The Endoventricular Circular Patch Plasty," *Seminars in Thoracic and Cardiovascular Surgery* 9(2):123-130, Apr. 1997.
Gelbart et al., "Method and Device for Closing Holes in Tissue," Office Action mailed Sep. 4, 2008, for U.S. Appl. No. 11/436,585, 8 pages.
Gelbart et al., "Method and Device for Closing Holes in Tissue," Amendment filed Sep. 22, 2008, for U.S. Appl. No. 11/436,585, 3 pages.

Gelbart et al., "Method and Device for Closing Holes in Tissue," Office Action mailed Jan. 2, 2009, for U.S. Appl. No. 11/436,585, 11 pages.

Gelbart et al., "Method and Device for Closing Holes in Tissue," Amendment filed Jan. 30, 2009, for U.S. Appl. No. 11/436,585, 5 pages.

Gelbart et al., "Method and Device for Closing Holes in Tissue," Amendment filed Jun. 2, 2009, for U.S. Appl. No. 11/436,585, 7 pages.

Gelbart et al., "Method and Device for Closing Holes in Tissue," Office Action mailed Jul. 7, 2009, for U.S. Appl. No. 11/436,585, 9 pages.

Gelbart et al., "Method and Device for Closing Holes in Tissue," Amendment filed Oct. 26, 2009, for U.S. Appl. No. 11/436,585, 13 pages.

International Search Report, mailed Jan. 8, 2007, for PCT/CA2006/001123, 5 pages.

International Search Report, mailed Sep. 4, 2009, for PCT/US2009/043612, 7 pages.

Jatene, "Left Ventricular Aneurysmectomy," *Journal of Thoracic and Cardiovascular Surgery* 89(3):321-331, 1985.

Lichtenstein, "Method and Apparatus for Percutaneous Reduction of Anterior-Posterior Diameter of Mitral Valve," Office Action mailed May 15, 2006, for U.S. Appl. No. 10/690,131, 9 pages.

Lichtenstein, "Method and Apparatus for Percutaneous Reduction of Anterior-Posterior Diameter of Mitral Valve," Office Action mailed Dec. 1, 2008, for U.S. Appl. No. 11/400,260, 10 pages.

Lichtenstein et al., "Method for Anchoring a Mitral Valve," U.S. Appl. No. 11/475,978, filed Jun. 28, 2006, 15 pages.

Lichtenstein et al., "Method for Anchoring a Mitral Valve," Office Action mailed May 1, 2009, for U.S. Appl. No. 11/475,978, 6 pages.

Lichtenstein et al, "Method for Anchoring a Mitral Valve," Amendment filed Aug. 31, 2009, for U.S. Appl. No. 11/475,978, 24 pages.

Lichtenstein et al, "Method for Anchoring a Mitral Valve," Office Action mailed Dec. 29, 2009, for U.S. Appl. No. 11/475,978, 7 pages.

Menicanti et al., "The Dor Procedure: What has Changed After Fifteen Years of Clinical Practice?" *Journal of Thoracic and Cardiovascular Surgery* 124(5):886-890, Nov. 2002.

Rivera et al., "Ventricular Aneurysms and Akinesis," *Cleveland Clinic Quarterly* 45(1):133-135, 1978.

Written Opinion, mailed Jan. 8, 2007, for PCT/CA2006/001123, 6 pages.

Written Opinion, mailed Sep. 4, 2009, for PCT/US2009/043612, 6 pages.

\* cited by examiner

METHOD FOR ANCHORING A MITRAL VALVE

FIELD OF THE INVENTION

The invention relates to minimally invasive cardiac surgery.

BACKGROUND OF THE INVENTION

The art of artificial heart valves is well known. Recently there is a strong interest in minimally invasive methods of replacing defective heart valves, and in particular in percutaneous deployment methods. In those procedures, the new valve is delivered and all the steps to install it, are performed via a fairly narrow catheter, typically 8-10 mm diameter.

Replacing major surgery with the small incision needed for inserting such a catheter is a major step in cardiac surgery.

The mitral valve is a particularly difficult case as the heart has an unfavorable geometry for anchoring a replacement valve. In conventional cardiac surgery the new valve is sutured to the tissue around the natural valve, which is surrounded by an annular ring of more rigid tissue known as the valve annulus.

This procedure is not practical for percutaneous surgery. The main object of the invention is to devise an anchoring method for a replacement mitral valve. A further object is making the method both reversible and percutaneous.

SUMMARY OF THE INVENTION

An artificial mitral valve is anchored in the left atrium by placing the valve between the annulus of the natural mitral valve and an artificial annulus. The artificial annulus is formed by inserting a tool into the coronary sinus, and adjusting the tool to force the wall of the left atrium to form an annulus above the artificial valve, thus locking the artificial mitral valve in place and forming a hemostatic seal. The artificial mitral valve can be held by compression from above or by circumferential compression from the tool. The compression can be released in order to remove the artificial mitral valve, if desired.

DESCRIPTION OF THE PREFERRED EMBODIMENT

Figure 1:
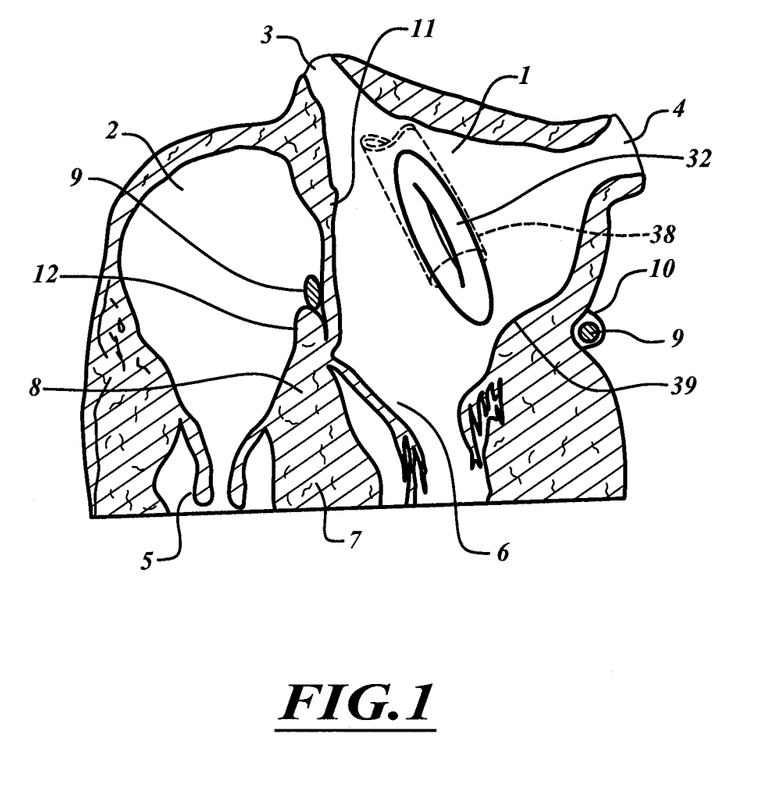
FIG. 1 is a longitudinal cross section of the heart, showing the left and right atriums.

Referring now to FIG. 1, the cross section of the upper part of the heart shows the left atrium 1, the right atrium 2, pulmonary veins 3 and 4, tricuspid valve 5 and mitral valve 6, interventricular septum 7, atrioventricular septum 8, coronary sinus 10, interartial septum 11, and tendon of Todaro 12. An artificial mitral valve 32 is introduced into the left atrium to replace a defective mitral valve 6. The artificial mitral valve 32 is of flexible construction in order to be deployed percutaneously via a catheter 38. For deployment the artificial mitral valve 32 is compressed into an elongated oval shape. The art of percutaneous deployment is well known in minimally invasive surgery. One way to deploy the artificial mitral valve 32 is to pass catheter 38 via septum 11, after entering the right atrium via the superior vena cava. An anchoring tool 9 is shown in FIG. 1 already inside the coronary sinus 10. The periphery of mitral valves 6 is less flexible and forms a shape 39 known as the mitral valve annulus.

Figure 2:
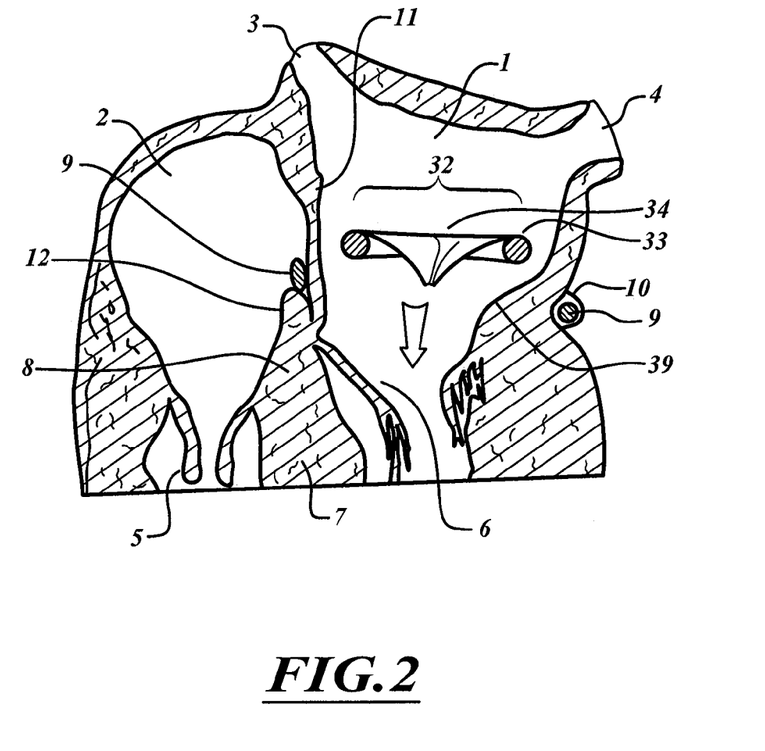
FIG. 2 is a longitudinal cross section of the heart as in FIG. 1, showing a deployed artificial mitral valve.

Referring now to FIG. 2, the artificial mitral valve 32 is allowed to expand to its normal form. The artificial mitral valve 32 comprises of very flexible leaflets 34, and a less flexible annulus 33. The overall shape of the artificial mitral valve 32 is matched to the area above the mitral valve annulus, which is generally "D" shaped. The cross section of the annulus can be round, oval, rectangular or any other shape suitable for forming a hemostatic seal when seated above the annulus 39 of the defective mitral valve 6. Annulus 33 can also be composed of multiple materials, some more rigid to better control the shape and some more flexible to help if forming a hemostatic seal. For example, annulus 33 can be made of soft silicone rubber with a Nitinol wire ring embedded in the annulus to control the shape of the ring. The leaflets 34 can be made of silicone rubber, Dacron or any other thin flexible material which is compatible with the heart. Artificial mitral valves capable of being delivered via a catheter are commercially available from Edwards Life Sciences (www.edwards.com).

At this stage the anchoring tool 9 is in the coronary sinus but the anchoring tool 9 is left in the relaxed and flexible position, as explained later on.

Figure 3:
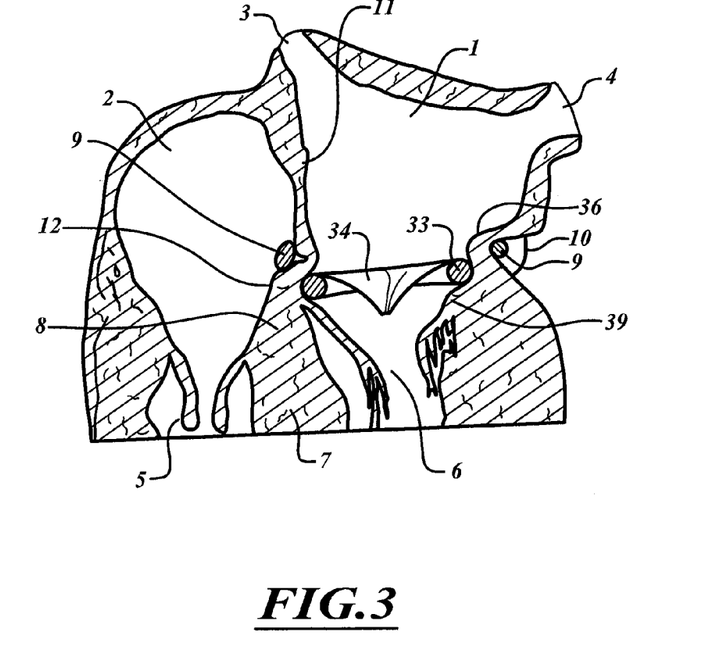
FIG. 3 is a longitudinal cross section of the heart as in FIG. 1, showing an artificial mitral valve anchored in place according to the invention.

After the artificial mitral valve 32 is placed at the final location above the defective valve 3, the artificial mitral valve 32 has to be anchored into place. The artificial mitral valve 32 is brought into the correct position by using the delivery catheter to push the artificial mitral valve 32 downwards (this is also aided by the downwards blood flow). To secure the artificial mitral valve 32 in place, a second annulus, similar to the natural annulus 39 of the mitral valve 6, is created above the artificial mitral valve 32 by a ring-like anchoring tool 9 shown in cross section in FIG. 3. When anchoring tool 9 is tightened it pulls in the outside wall of left atrium 1 as well as interartial septum 11 to form an almost full ring 36 around the valve annulus 33. This locks the artificial mitral valve 32 between the natural annulus 39 of mitral valve 6 and an artificial annulus 36. By further tightening anchoring tool 9 a hemostatic seal is established. Since valve annulus 33 is flexible (as is anchoring tool 9) it will conform to the exact shape of the natural annulus 39. Inside the right atrium, tool 9 is placed against the interartial septum 11 just above tendon of Todaro 12.

Figure 4:
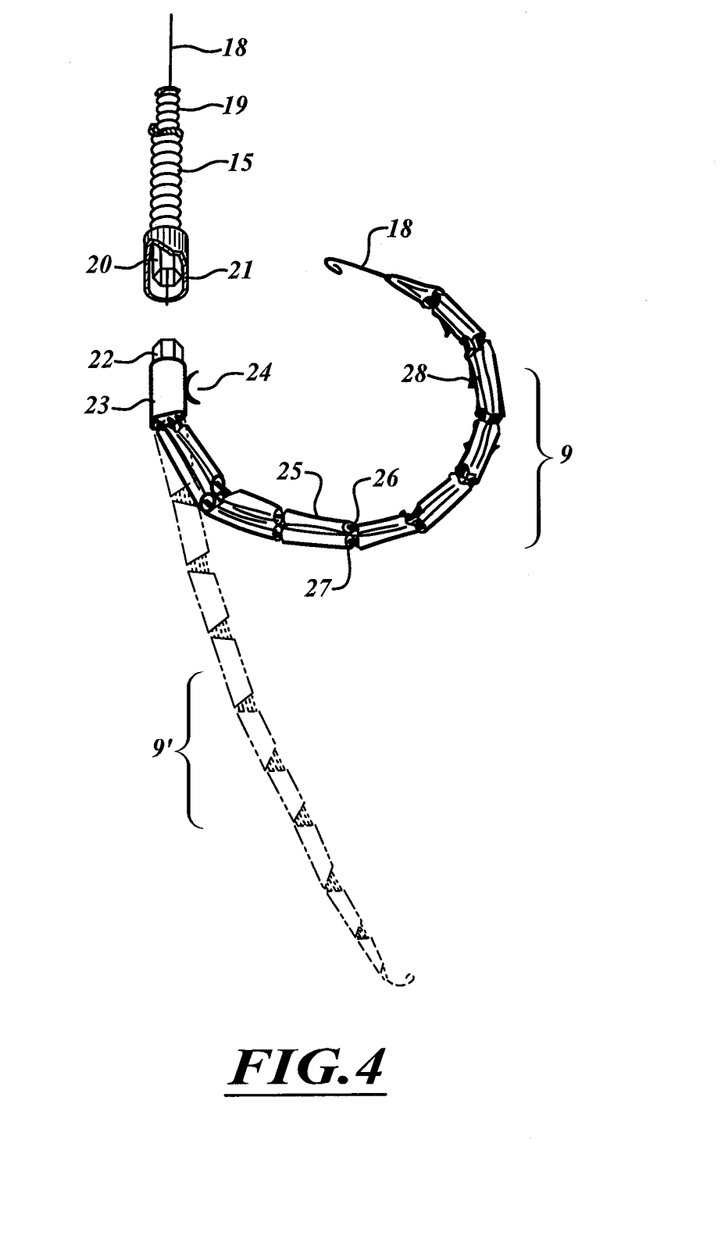
FIG. 4 is a general view of the anchoring tool.

Details of anchoring tool 9 are shown in FIG. 4. Anchoring tool 9 is made of rigid links 25 connected by two flexible cables 26 and 27. Protrusions or barbs 28 can be added to increase anchoring in the coronary sinus. A barb 24 is mounted on end piece 23. This barb is covered by tube 21 of adjustment tool 15. When tube 21 is detached from end piece 23, barb 24 springs open and secures the position of anchoring tool 9 relative to septum 11 (shown in FIG. 1). The shape of anchoring tool 9 is adjusted by tensioning cable 26 by turning screw 22 using matching socket 21 connected to inner flexible tube 19. Both anchoring tool 9 and flexible tube 15 have a hole for guide wire 18. Flexible tube 19 can rotate freely inside flexible adjustment tool 15. Both adjustment tool 15 and inner flexible tube are made of metal bellows type hose or of a braided hose, as these type hoses are torsionally stiff but easy to bend. It is desirable to make screw 22 and socket 20 of a ferromagnetic material, and provide a small rare-earth magnet (not shown) inside socket 20. This facilitates locating screw 22 if adjustment tool 15 has to be re-connected to anchoring tool 9 inside the heart.

Figure 5:
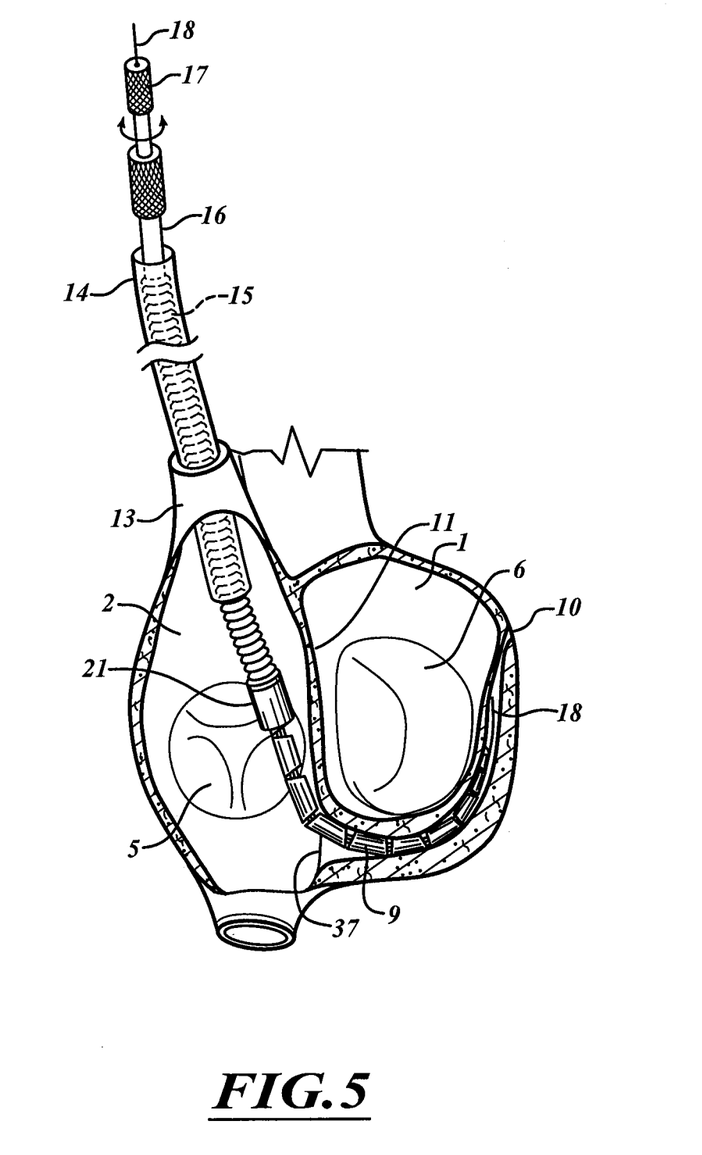
FIG. 5 is a schematic view showing the use of the anchoring tool in a percutaneous operation.

Referring now to FIG. 5 and FIG. 4, the percutaneous use of an embodiment of the invention is shown. Anchoring tool 9 is attached to flexible adjustment tool 15 and is inserted into the right atrium 2 via catheter 14, typically through the superior vena cava 13 over a guide wire 18. Guide wire 18 is inserted first, via ostium 37, all the way to the end of the coronary sinus 10. Tools 9 and 15 are guided by the wire 18. Anchoring tool 9 can be bent into shape by turning knob 17 while holding shaft 16. Turning knob 17 will turn socket 20 and tighten cable 26. To release adjustment tool 15, knob 17 is pressed into shaft 16 causing tool 9 to be ejected from tube 21 and embed barb 24 in septum 11. The operation is fully reversible as long as guide wire 18 is in place. It is even possible to re-adjust or remove anchoring tool 9 at a later date, if socket 20 can be lined up with screw 22. This is assisted by magnetic attraction, as explained earlier. The reversibility of the operation is a major advantage should the artificial mitral valve 32 need to be removed.

The same tool can be used both as an adjustment tool for controlling regurgitation in a natural mitral valve and as an anchoring tool for an artificial mitral valve. This is important as in many cases an adjustment can correct the problem in the natural mitral valve, without need for installing an artificial mitral valve. At a later date an artificial mitral valve may be required. In such a case, anchoring tool 9 simply needs to be loosened, an artificial mitral valve installed and anchoring tool 9 re-tightened.

Figure 6A:
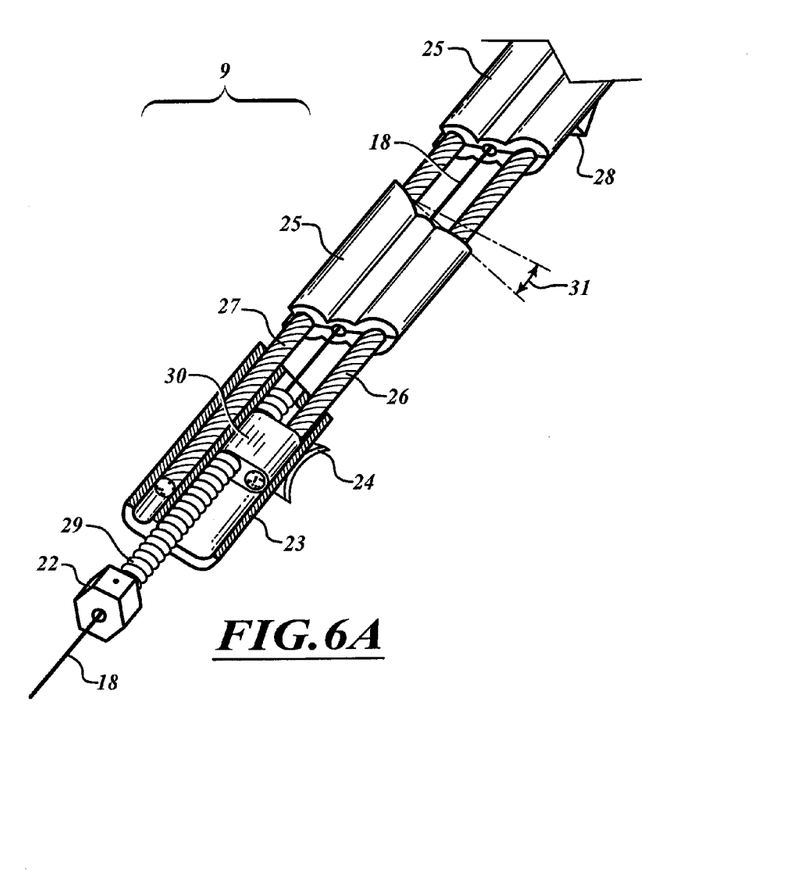
FIG. 6A is a partial isometric view of the anchoring tool.
Figure 6B:
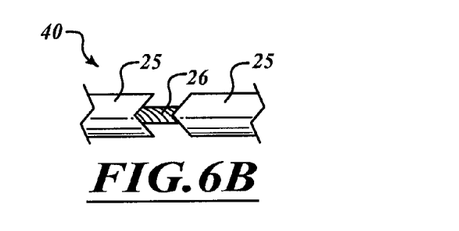
FIG. 6B is a side elevational view of a portion of the anchoring tool.

A more detailed view of anchoring tool 9 is given in FIGS. 6A and 6B. Each one of links 25 are cut at an angle 31. Angles 31 and length of links 25 determine the final shape of anchoring tool 9 when cable 26 is fully tightened. In order to keep links 25 in a single plane, the ends are cut in a V-shape as shown in insert drawing 40, which depicts a side view of links 25. The V shaped cut can be aligned with the longitudinal axis, as shown in 40, or can form an arbitrary angle to it. In such a case anchoring tool 9 will acquire a three-dimensional shape when tightened rather than fit in a single plane. Tightening screw 22 pulls nut 30 and tensions cable 26, causing anchoring tool 9 to tighten towards the final shape. The cross section of links 25 is designed to allow maximal blood flow in the coronary sinus. Cable 26 is permanently attached to nut 30 and to the last link (not shown), which is the link furthest away from end piece 23. Cable 27 is permanently attached to the last link but not attached to end piece 23 in order to accommodate the change in length when anchoring tool 9 is changing from straight to curved. When cable 26 is loosened, anchoring tool 9 is very flexible, similar to a chain. When cable 26 is fully tight, anchoring tool 9 can exert considerable force (a few Kg) in the radial direction.

By the way of example, anchoring tool 9 is made of type 316 stainless steel, with links 25 having a cross section of about 2×3 mm, and a length of about 12 mm each. Each links has three holes about 1 mm diameter each. Cables 26 and 27 are made of stainless steel as well and have an outside diameter of about 0.8 mm. Screw 22 is made of 400 series stainless (to be magnetic) and is 2 mm diameter with 3 mm hex head.

The term "annulus" in this disclosure has to be broadly interpreted. It need not be a complete circle, as anchoring tool 9 encircles the majority of the artificial mitral valve circumference but not all of it, due to the presence of the aortic valve. The term "artificial annulus" should be understood as any arc-like retention feature formed by anchoring tool 9. Also, while the preferred embodiment shows the artificial annulus formed above the artificial mitral valve, it is obvious that the artificial annulus can be used to anchor the artificial mitral valve even without being above it. By the way of example, the periphery of the artificial mitral valve can have a groove and the artificial annulus can engage this groove. In a different embodiment the base of the artificial mitral valve can be wider than the top part, thus allowing anchoring by an artificial annulus. It is also clear that the anchoring tool 9 need not be made of individual links. The anchoring tool 9 can be made of an elastic material such as Nitinol and rely on the elastic force to form the artificial annulus. While the term "anchoring" in this disclosure implies forming a hemostatic seal between the artificial valve annulus and the existing mitral vale annulus, it is understood that the seal need not be perfect to practice the invention, as any small gaps tend to seal themselves over time due to formation of scar tissue and deposits. A further improvement can be in the form of adding magnets to the artificial valve annulus and adding ferromagnetic material to anchoring tool 9. This helps align the artificial mitral valve 32 with the artificial annulus. While the force of the magnets may be insufficient to retain the artificial mitral valve 32, it is sufficient to hold in the correct position until anchoring tool 9 is tightened.

Figure 7:
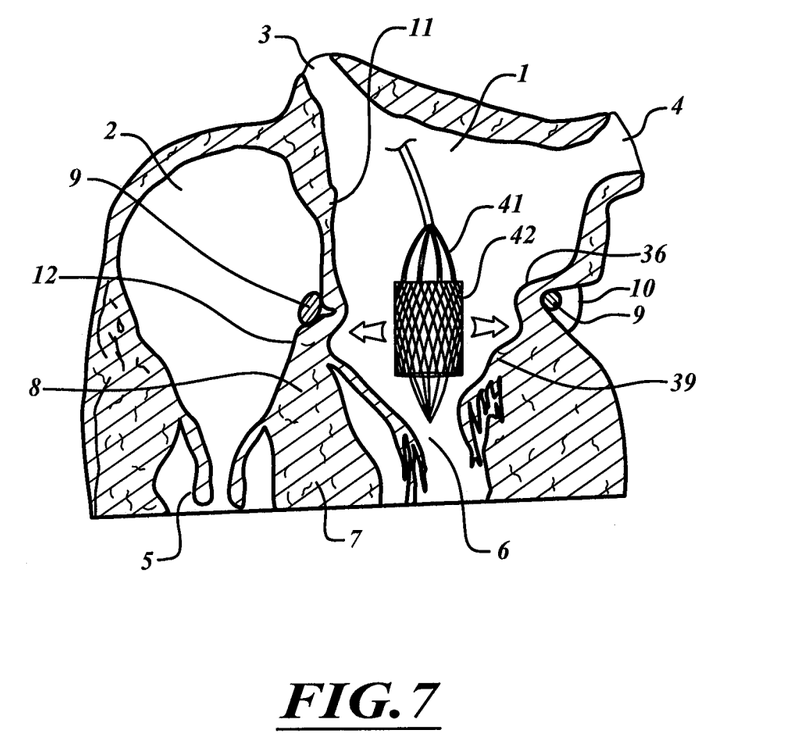
FIG. 7 is a schematic view showing the use of the invention in anchoring a balloon expandable valve.

An alternate way of using the artificial annulus is to use it as an anchoring base for a balloon expandable valve. Balloon expandable valves are well known in the art and are used, for example, as replacement aortic valves. Until now they were not used as mitral valves since there was no sufficiently rigid surface to expand the balloon against. FIG. 7 shows use of an anchoring tool 9 to form a rigid artificial annulus 36, then expansion of a balloon mounted valve 42, mounted on balloon 41, into the rigid structure that was formed.

What is claimed is:

1. A device to replicate a function of a natural mitral valve in a left atrium of a heart, at least partially about which natural mitral valve a coronary sinus of said heart extends, the device comprising:

an artificial mitral valve insertable inside an opening formed by the natural mitral valve in the left atrium of said heart; and     an elongate member having a flexible state and a more rigid state, said elongated member being at least partially insertable into the coronary sinus in the flexible state such that the elongate member at least partially encircles a portion of the artificial mitral valve, and which elongate member forms an artificial annulus in the more rigid state to physically secure the artificial mitral valve in the opening.

2. A device as in claim 1 wherein said elongate member is adjustable and removable during the installation of the device in the heart as well as at a later date.

3. A device as in claim 1 wherein said elongate member comprises a plurality of rigid links and a cable that connects the rigid links, and a tension of said cable is adjustable.

4. A device as in claim 1 wherein the elongate member is sized to be delivered percutaneously by a detachable adjustment tool.

5. A device as in claim 1 wherein said elongate member is sized to be delivered via a catheter using an adjustment tool, and said elongate member is equipped with at least one elastic barb, said barb being exposed by detaching said elongate member from said adjustment tool.

6. A device as in claim 1 wherein said elongate member is sized to be delivered via a catheter by the use of an adjustment tool, said elongate member attachable to said adjustment tool at least partially by a magnetic force.

7. A device as in claim 1 wherein said device comprises a magnetic coupler to aid in positioning said artificial mitral valve.

8. A device as in claim 1 wherein said artificial mitral valve is secured in the opening by the artificial annulus without sutures between said artificial mitral valve and said heart.

9. A device to replicate a function of a natural mitral valve in a left atrium of a heart, a coronary sinus of the heart forming a path extending at least partially about the natural mitral valve, the device comprising:
   an artificial mitral valve percutaneously insertable inside an opening formed by the natural mitral valve of the heart; and
   an elongate member having a flexible state and a more rigid state, the elongated member sized in the flexible state to be received by a catheter for percutaneous insertion in the coronary sinus, which elongate member forms an artificial annulus in the coronary sinus with a dimension that is percutaneously adjustable to physically secure the artificial mitral valve in the opening without any sutures between the artificial mitral valve and the heart.

10. A device as in claim 9 wherein the artificial mitral valve and the elongate member are each configurable to be received by a catheter.

11. A device as in claim 9 wherein said elongate member comprises a plurality of rigid links and a cable that connects the rigid links, a tension of the cable is adjustable to transition the elongate member between the flexible state and the more rigid state.

12. A device as in claim 9 wherein the elongate member applies a radially inward force to an annulus of the artificial mitral valve via the coronary sinus when the elongate member is tensioned into the more rigid state during use to secure the annulus of the artificial valve between a natural annulus of the natural mitral valve and the artificial annulus formed by the elongate member.

13. A device as in claim 9 wherein the elongate member has a tension adjustment coupler proximate a first end thereof, movement of which in one direction increases a tension in the elongate member and movement of which is another direction decreases the tension in the elongate member.

14. A device as in claim 13 wherein the tension adjustment coupler is part of a magnetic coupler assembly that magnetically mates with a portion of an adjustment tool which portion is at least partially percutaneously receivable in the heart.

15. A device as in claim 13 wherein the elongate member has a barb proximate a second end thereof.

16. A device to replicate a function of a natural valve in a heart, the device comprising:
   an artificial valve percutaneously insertable inside an opening formed by the natural valve of the heart;
   an elongate member having a flexible state and a more rigid state, the elongated member sized in the flexible state to be received by a catheter for percutaneous insertion in a blood vessel, which elongate member is percutaneously adjustable to physically secure the artificial valve in the opening without any sutures between the artificial valve and the heart; and
   a tool which can be manipulated to adjust the elongate member percutaneously and which is selectively detachable from a portion of the elongate member.

* * * * *